(12) United States Patent
Didomenico et al.

(10) Patent No.: US 7,164,132 B2
(45) Date of Patent: Jan. 16, 2007

(54) MULTILANE REMOTE SENSING DEVICE

(75) Inventors: John Didomenico, Tucson, AZ (US);
James Johnson, Tucson, AZ (US);
Donald H. Stedman, Denver, CO (US);
Gary A. Bishop, Louisville, CO (US);
W. John Williams, Littleton, CO (US)

(73) Assignee: Envirotest Systems Corp., East Granby, CT (US)

( * ) Notice: Subject to any disclaimer, the term of this patent is extended or adjusted under 35 U.S.C. 154(b) by 0 days.

(21) Appl. No.: 09/907,451

(22) Filed: Jul. 18, 2001
(Under 37 CFR 1.47)

(65) Prior Publication Data
US 2002/0092988 A1 Jul. 18, 2002

Related U.S. Application Data

(63) Continuation of application No. 09/579,475, filed on May 26, 2000, which is a continuation of application No. 09/428,992, filed on Oct. 29, 1999, now abandoned.

(60) Provisional application No. 60/106,281, filed on Oct. 30, 1998.

(51) Int. Cl.
*G01N 21/00* (2006.01)
(52) U.S. Cl. .................................. 250/338.5
(58) Field of Classification Search .............. 250/338.5
See application file for complete search history.

(56) References Cited

U.S. PATENT DOCUMENTS

| 3,593,023 A | 7/1971 | Dodson et al. |
| 3,696,247 A | 10/1972 | McIntosh et al. |
| 3,735,127 A * | 5/1973 | Astheimer ................. 250/346 |
| 3,743,426 A | 7/1973 | Steinberg |
| 3,908,167 A | 9/1975 | Hulls et al. |
| 3,957,372 A | 5/1976 | Jowett et al. |
| 3,958,122 A | 5/1976 | Jowett et al. |

(Continued)

FOREIGN PATENT DOCUMENTS

WO    WO 91/20067    12/1991

(Continued)

OTHER PUBLICATIONS

Technical Proposal—"Vehicle Inspection Instrumentation"; submitted to California Air Resources Board; Sep. 1, 1971, Lockheed Palo Alto Research Laboratory, Lockheed Missiles & Space Company—A Group Division of Lockheed Aircraft Corporation, Palo Alto, California.

(Continued)

*Primary Examiner*—David Porta
*Assistant Examiner*—Shun Lee
(74) *Attorney, Agent, or Firm*—Pillsbury Winthrop Shaw Pittman, LLP

(57) ABSTRACT

A remote sensing device is provided to detect the emissions of passing vehicles. Preferably, the device detects the emissions of individual vehicles traveling on a roadway of more than one traffic lane. The remote sensing device may preferably detect the emissions due to an individual vehicle in situations where more than one vehicle is present. The device is capable of determining which sensed emission data corresponds to which vehicle exhaust plume.

34 Claims, 7 Drawing Sheets

U.S. PATENT DOCUMENTS

| | | | |
|---|---|---|---|
| 3,973,848 | A | 8/1976 | Jowett et al. |
| 4,160,373 | A | 7/1979 | Fastaia et al. |
| 4,390,785 | A | 6/1983 | Faulhaber et al. |
| 4,480,191 | A | 10/1984 | Karpowycz |
| 4,490,043 | A | 12/1984 | Cramp |
| 4,544,273 | A | 10/1985 | Berndt |
| 4,560,873 | A | 12/1985 | McGowan et al. |
| 4,663,961 | A | 5/1987 | Nelson et al. |
| 4,719,360 | A | 1/1988 | Kontani et al. |
| 4,746,218 | A | 5/1988 | Lord, III |
| 4,765,961 | A | 8/1988 | Schiff et al. |
| 4,795,253 | A | 1/1989 | Sandridge et al. |
| 4,810,884 | A | 3/1989 | Carlson |
| 4,818,705 | A | 4/1989 | Schneider et al. |
| 4,829,183 | A | 5/1989 | McClatchie et al. |
| 4,924,095 | A | 5/1990 | Swanson, Jr. |
| 4,990,780 | A | 2/1991 | Lee et al. |
| 4,999,498 | A | 3/1991 | Hunt et al. |
| 5,060,505 | A | 10/1991 | Tury et al. |
| 5,099,680 | A | 3/1992 | Fournier et al. |
| 5,105,651 | A | 4/1992 | Gutmann |
| 5,129,257 | A | 7/1992 | Carduner et al. |
| 5,184,017 | A | 2/1993 | Tury et al. |
| 5,210,702 | A | 5/1993 | Bishop et al. |
| 5,246,868 | A | 9/1993 | Busch et al. |
| 5,252,828 | A | 10/1993 | Kert et al. |
| 5,306,913 | A | 4/1994 | Noack et al. |
| 5,319,199 | A | 6/1994 | Stedman et al. |
| 5,332,901 | A | 7/1994 | Eckles et al. |
| 5,343,043 | A | 8/1994 | Johnson |
| 5,371,367 | A | 12/1994 | DiDomenico et al. |
| 5,373,160 | A | 12/1994 | Taylor |
| 5,386,373 | A | 1/1995 | Keeler et al. |
| 5,401,967 | A | 3/1995 | Stedman et al. |
| 5,416,711 | A * | 5/1995 | Gran et al. .................. 701/117 |
| 5,418,366 | A | 5/1995 | Rubin et al. |
| 5,451,787 | A | 9/1995 | Taylor |
| 5,489,777 | A | 2/1996 | Stedman et al. |
| 5,498,872 | A | 3/1996 | Stedman et al. |
| 5,572,424 | A | 11/1996 | Kellogg et al. |
| 5,583,765 | A | 12/1996 | Kleehammer |
| 5,589,629 | A | 12/1996 | Quinn |
| 5,591,975 | A | 1/1997 | Jack et al. |
| 5,621,166 | A | 4/1997 | Butler |
| 5,644,133 | A | 7/1997 | Didomenico et al. |
| 5,693,872 | A | 12/1997 | Quinn |
| 5,719,396 | A | 2/1998 | Jack et al. |
| 5,726,450 | A | 3/1998 | Peterson et al. |
| 5,731,510 | A | 3/1998 | Jones et al. |
| 5,753,185 | A | 5/1998 | Mathews et al. |
| 5,797,682 | A | 8/1998 | Kert et al. .................. 374/123 |
| 5,812,249 | A * | 9/1998 | Johnson et al. ............... 356/28 |
| 5,831,267 | A | 11/1998 | Jack et al. |

FOREIGN PATENT DOCUMENTS

| | | |
|---|---|---|
| WO | WO 98/39248 | 9/1998 |

OTHER PUBLICATIONS

Hoshizaki, et al., Final Report—"Vehicle Inspection Instrumentation"; submitted to California Air Resources Board; Jun. 1973, Lockheed Palo Alto Research Laboratory, Lockheed Missiles & Space Company—A Group Division of Lockheed Aircraft Corporation, Palo Alto, California.

http://www.epa.gov/otaq/15-remot.htm; "Remote Sensing: A Supplemental Tool for Vehicle Emission Control," Aug. 1993, EPA 400-F-92-017, Fact Sheet OMS-15; 4 pages.

Lucien W. Chaney, "The Remote Measurement of Traffic Generated Carbon Monoxide, APCA Note-Book," Journal of the Air Pollution Association; Copyright 1983; 3 pages.

Paul Stockwell, "Tunable Diode Laser Systems Break New Ground in Water Vapour Analysis"; IMA Ltd., Unit Newall Hall Park, Otley, West Yorkshire, United Kingdom; [undated]; 8 pages.

Mark G. Allen, "Diode Laser Absorption Sensors for Gas Dynamic and Combustion Flows," Copyright 1998 Measurement Science and Technology 9; 61 pages, 545-562.

Kerry L. Swayne, "Infrared Remote Sensing of On-Road Motor Vehicle Emissions in Washington State," Mar. 1999, Air Quality Program, Washington State Department of Ecology, Washington; Publication #99-204; 20 pages.

Gary A. Bishop, et al., "IR Long-Path Photometry: A Remote Sensing Tool for Automobile Emissions," 1989; reprinted from Analytical Chemistry, 61. 671A; 1989; 6 pages.

Gary A. Bishop, et al., "Oxygenated Fuels, A Remote Sensing Evaluation," SAE Technical Paper Series; Copyright 1989 Society of Automotive Engineers, Inc.; 7 pages.

Robert D. Stephens, "Remote Sensing Data and a Potential Model of Vehicle Exhaust Emissions," Nov. 1994, vol. 44, Journal of Air & Waste Management Association, pp. 1284-1292.

"An Analysis of On-Road Remote Sensing as a Tool for Automobile Emissions Control," Final Report Prepared by University of Denver Chemistry Department, Colorado, Mar. 1990; 174 pages; prepared for Illinois Department of Energy and Natural Resources.

Robert D. Stephens, et al., "Remote Sensing Measurements of In-Use Vehicle Carbon Monoxide and Hydrocarbon Exhaust Emissions," Environmental Science Department, Michigan, to be presented to Society of Automotive Engineers Government/Industry Metting, Washington, D.C., May 15, 1991; 9 pages.

Thomas C. Austin, et al., "An Evaluation of "Remote Sensing" for the Measurement of Vehicle Emissions," prepared for The California Air Resources Board and The California I/M Review Committee, Aug. 28, 1990, 30 pages; prepared by Sierra Research, Inc., California.

Robert D. Stephens, et al., "Remote Sensing Measurements of Carbon Monoxide Emissions from On-Road Vehicles," Copyright Jan. 1991, Air & Waste Management Association, vol. 41, No. 1, pp. 39-46.

Donald H. Stedman, et al., "Remote Sensing of On-Road Vehicle Emissions," Final Report to Coordinating Research Council, The university of Denver, Jan. 6, 1992, 21 pages.

Peter Popp, et al., "Development of a High-Speed Ultraviolet Spectrophotometer Capable of Real-Time NO and Aromatic Hydrocarbon Detection in Vehicle Exhaust," Department of Chemistry, University of Denver, Colorado, Prepared for Proceedings of the 7th CRC On-Road Vehicle Emissions Workshop, San Diego, California, Apr. 9-11, 1997; 10 pages.

John Didomenico, et al., "Preliminary Results from Cold Start Sensor Testing," Presented to 7th CRC On-Road Vehicle Emissions Workshop, San Diego, California Apr. 9-11, 1997; 1 page.

Gary A. Bishop, et al., "Enhancements of Remote Sensing for Vehicle Emissions in Tunnels," Air & Waste Management Association, vol. 44, Feb. 1994, pp. 169-175.

Paul Leonard Guenther, "Contributions to On-Road Remote Sensing of Automobile Exhaust, " A Thesis Presented to the Faculty of Natural Sciences, Mathematics, and Engineering, University of Denver, Jun. 1992, 95 pages.

Donald H. Stedman, et al., "On-Road Remote Sensing of CO and HC Emissions in California," Prepared for Research Division, California Air Resources Board, Sacramento, CA, submitted by University of Denver Chemistry Department, Feb. 1994, 136 pages.

"Unstaffed On-Road Emissions Measurement Systems Services," Prepared by Parsons Engineering Science Inc., Pasadena, California, Sep. 1995.

"Proposal/Quote for Unstaffed On-Road Emissions Measurement Systems Services" in response to Phase IV—RFQ #94/95-003, prepared by Remote Sensing technologies, Inc. delivered to Department of Consumer Affairs, Bureau of Automotive Repair, Sacramento, California, Sep. 1, 1995.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Dec. 9, 1997, prepared by General Motors R&D Center, Michigan; 20 pages.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Mar. 24, 1998, "Appendix E. University of Denver Remote Sensing Observation of Smoking Vehicles," prepared by General Motors R&D Center, Michigan; 20 pages.

Robert D. Stephens, et al., "Remote Sensing of Carbon Monoxide Emissions from On-Road Vehicles," Environmental Science Department, General Motors Research Laboratories, Michigan for presentation to Air and Waste Management Association, NC, May 1, 1990, 46 pages.

"Description and Documentation for Interim Vehicle Clean Screening Credit Utility," Draft Report, United States Environmental Protection Agency, May 1998, 40 pages.

David S. E. Petherick, "Ontario's Indoor, Controlled-Mode Remote Sensing I/M Prescreen Concept," Ministry of Transportation of Ontario, Copyright 1996 Society of Automotive Engineers, Inc., 9 pages.

P. A. Walsh, et al., "Texas 1996 Remote Sensing Feasibility Study," Final Report, prepared for Texas Natural Resource Conservation Commission, Austin, Texas, Aug. 29, 1997, prepared by Desert Research Institute, Energy and Environmental Engineering Center, Reno, Nevada, 9 pages.

"On Road Emissions Measurement System—Specifications," Bureau of Automotive Repair, Aug. 30, 1999, Revision—J, 15 pages.

Craig S. Rendahl, "Further Analysis of Wisconsin's Remote Vehicle Emissions Sensing Feasibility Studies," "Quality Control Efforts of Remote Vehicle Emissions Sensing," and "Data Handling and Validation from Wisconsin's Remote Vehicle Emissions Sensing Studies," Presented at the Air & Waste Management Annual Measurement of Toxics and Related Pollutants Conference, Research Triangle Park, North Carolina, May 1996, 34 pages.

James D. Peterson, et al., "Find and Fix the Polluters", Chemtech, Jan. 1992, Copyright 1992 American Chemical Society, 7 pages, 47-53.

RSD 1000 Operator's Manual (Preliminary), Remote Sensing Technologies, IFB No. 94019, Jun. 1993, 66 pages.

RSD 1000 Remote Sensing Device Information Package to Mr. Wolf Klassen, Department of Natural Resources, Presented by Dennis L. Smith, Feb 24, 1993, 123 pages.

Donald H. Stedman, "Automobile Carbon Monoxide Emission", Environmental Science & Technology, vol. 23, No. 2, 1989, pp. 147-149.

Michael D. Koplow, et al., "Characterization of On-Road Vehicl NO Emissions by Means of a TILDAS Remote Sensing Instrument", Published by the Coordinating Research Council, Published for the 7th CRC On-Road Vehicle Emissions Workshop, Mar. 11, 1997, pp. 1-25.

Scott E. McLaren, et al., "Comparison of an Open Path UV and FTIR Spectrophotometer", Published by the Air & Waste Management Association, Published for Presentation at the 85th Annual Meeting & Exhibition, Kansas City, Missouri, Jun. 21-26, 1992, pp. 1-10.

"Developing an Inspection/Maintenance Program for Alternatively-Fueled Vehicles", Third Interim Report Submitted to the California Bureau of Automotive Repair, Submitted by Radian Corporation, Apr. 20, 1993, 147 pages.

Iain Frederick McVey, "Development of a Remote Sensor for Mobile Source Nitric Oxide", A Thesis Presented to the Faculty of Natural Sciences, Mathematics, and Engineering, University of Denver, Nov. 1992, 111 pages.

S. P. Beaton, et al., "Emission Characteristics of Mexico City Vehicles", Journal of the Air & Waste Management Association, vol. 42, No. 11, Nov. 1992, pp. 1424-1429.

Douglas R. Lawson, et al., "Emissions from In-Use Motor Vehicles in Los Angeles: A Pilot Study of Remote Sensing and the Inspection and Maintenance Program", Journal of the Air & Waste Management Association, vol. 40, No. 8, Aug. 1990, pp. 1096-1105.

Yi Zhang, et al., "Enhancement of Remote Sensing for Mobile Source Nitric Oxide", Journal of the Air & Waste Management Association, vol. 46, Jan. 1996, pp. 25-29.

Donald H. Stedman, et al., "Evaluation of a Remote Sensor for Mobile Source CO Emissions", U.S. Environmental Protection Agency, CR-815778-01-0, Report No. EPA/600/4-90/032, Jan. 1991, 90 pages.

James Butler, et al., "Factors Affecting the NDIR Measurement of Exhaust Hydrocarbons", Published by the Coordinating Research Council, Published for the CRC 5th On-Road Vehicle Emissions Workshop, 1995, 16 pages.

Scott E. McLaren, et al., "Flux Measurements Using Simultaneous Long Path Ultraviloet and Infrared Spectroscopy", Published by the Air & Waste Management Association, Published for Presentation at the 83rd Annual Meeting & Exhibition, Pittsburgh, Pennsylvania, Jun. 24-29, 1990, 7 pages.

Gary A. Bishop, et al., "Infrared Emission and Remote Sensing", Journal of the Air & Waste Management Association, vol. 42, No. 5, May 1992, pp. 695-697.

Donald H. Stedman, et al., "NOx Data by Remote Sensing", Published by the Coordinating Research Council, Published for the 5th CRC On-Road Vehicle Emissions Workshop, Apr. 3-5, 1995, 16 pages.

Donald H. Stedman, et al., "On-Road Carbon Monoxide and Hydrocarbon Remote Sensing in the Chicago Area", Final Report Prepared by University of Denver Chemistry Department, Prepared for Illinois Department of Energy and Natural Resources, Office of Research and Planning, Illinois Contract AQ 40, Project 91/122, Report No. ILENR/RE-AQ-91/14, Oct. 1991, pp. 1-70.

Gary A. Bishop, et al., "On-Road Carbon Monoxide Emission Measurement Comparisons for the 1988-1989 Colorado Oxy-Fuels Program", Environmental Science & Technology, vol. 24, No. 6, 1990, pp. 843-847.

Donald H. Stedman, et al., "On-Road CO Remote Sensing in the Los Angeles Basin", Final Report Prepared for the Research Division, California Air Resources Board, Submitted by University of Denver Chemistry Department, Aug. 1991, Contract No. A932-189, 70 pages.

Scott Mclaren, "Open Path Spectrometers for Atmospheric Monitoring", A Dissertation Presented to the Faculty of Natural Sciences, Mathematics and Engineering, Nov. 1995, 170 pages.

Carol E. Lyons, et al., "Remote Sensing Enhanced Motor Vehicle Emissions Control for Pollution Reduction in the Chicago Metropolitan Area: Siting and Issue Analysis", Final Report Prepared by University of Denver Atmospheric Science Center, Prepared for Illinois Department of Energy and Natural Resources, Office of Research and Planning, Illinois Contract AQ 30, Project 90/009, Report No. ILENR/RE-AQ-91/15, Oct. 1991, pp. 1-65.

Brett C. Singer, et al., "Scaling of Infrared Remote Sensor Hydrocarbon Measurements for Motor Vehicle Emission Inventory Calculations", Environmental Science & Technology, vol. 32, No. 21, 1998, pp. 3241-3248.

Jose Luis Jimenez-Palacios, "Understanding and Quantifying Motor Vehicle Emissions with Vehicle Specific Power and TILDAS Remote Sensing", A Dissertation Presented to the Department of Mechanical Engineering, Feb. 1999, 360 pages.

"Vehicle Inspection Instrumentation", Published by the Lockheed Missiles and Space co., Inc., Report No. ARB-R-643-73-26, Jun. 30, 1973, 99 pages.

Yi Zhang, et al., "Worldwide On-Road Vehicle Exhaust Emissions Study by Remote Sensing", Environmental Science & Technology, vol. 29, No. 9, 1995, pp. 2286-2294.

Masayuki Adachi, et al., "Automotive Emission Analyses Using FTIR Spectrophotometer", Published by the Society of Automotive Engineers, SAE# 920723, Feb. 1, 1992, pp. 820-827.

Lucian W. Chaney, "The Remote Measurement of Traffic Generated Carbon Monoxide", Journal of the Air Pollution Control Association, vol. 33, No. 3, Mar. 1983, pp. 220-222.

Robert D. Stephens, et al., "An Experimental Evaluation of Remote Sensing Based Hydrocarbon Measurements: A Comparison to FID Measurements", Journal of the Air & Waste Management Association, vol. 46, Feb. 1996, pp. 148-158.

Hakan Axelsson, et al., "Measurement of Aromatic Hydrocarbons with the DOAS Technique", Applied Spectroscopy, received Apr. 18, 1994, accepted May 3, 1995, vol. 49, No. 9, 1995, pp. 1254-1260.

Gary A. Bishop, et al., "Method Comparisons of Vehicle Emissions Measurements in the Fort McHenry and Tuscarora Mountain Tunnels", *Atmospheric Environment*, first received Dec. 2, 1993 and in final form Nov. 10, 1994, vol. 30, No. 12, 1996, pp. 2307-2316.

Peter John Popp, "Remote Sensing of Nitric Oxide Emissions from Planes, Trains and Automobiles", A Dissertation Presented to the Faculty of Natural Sciences, Mathematics and Engineering, Aug. 1999, 170 pages.

John E. Sigsby, Jr., et al., "Volatile Organic Compound Emissions from 40 In-Use Passenger Cars", *Environmental Science & Technology*, received for review Oct. 22, 1984, revised manuscript received Sep. 30, 1986, accepted Dec. 29, 1986, vol. 21, No. 5, 1987, pp. 466-475.

\* cited by examiner

MULTILANE REMOTE SENSING DEVICE

This application is a continuation of application Ser. No. 09/579,475, filed May 26, 2000, which is a continuation of prior Application Ser. No. 09/428,992, filed Oct. 29, 1999, now abandoned which claims priority from Provisional Application Ser. No. 60/106,281, filed Oct. 30, 1998.

FIELD OF THE INVENTION

This invention relates to remote sensing of vehicle emissions on a multiple lane roadway.

BACKGROUND OF THE INVENTION

Remote emission detection systems in general are known. Typically, existing systems are used to detect emission data from a single vehicle traveling in a single lane of traffic such as an exit ramp from a highway. Such a configuration restricts the locations at which the device can be employed and limits the number of vehicles that can be processed in a given time period.

Another drawback of existing remote emission detection systems that it is difficult to correctly associate each vehicle with its emission data when more than one vehicle is present. For example, if multiple vehicles are present at the sensing location, each vehicle's exhaust plume may contribute emissions. Existing systems are not able to differentiate among several exhaust plumes.

These and other drawbacks exist.

SUMMARY OF THE INVENTION

An object of the invention is to overcome these and other drawbacks in existing devices.

Another object of the invention is to provide a multiple lane remote emission sensing system that increases the number of potential sites for remote emission testing.

Another object is to provide a multilane remote emission detection system that is able to distinguish the emissions due to a particular vehicle under conditions where more than one vehicle exhaust plume may be present.

Another object of certain embodiments of the invention is to provide a multilane remote emission detector that is substantially unobtrusive and does not interfere with vehicle traffic.

Another object of certain embodiments of the invention is to provide a multilane remote emission detection system that does not draw the attention of, or distract, motorists.

These and other objects of the invention are accomplished by various embodiments of the invention. Accordingly, there is provided a system and method for remotely detecting emissions from individual vehicles traveling on a multilane roadway. The remote detection system preferably comprises a source of radiation to be directed through the exhaust plume of a passing vehicle, at least one detector to detect the source radiation which remains after passing through the exhaust plume and a processor to process the data recorded by the detector and associate such data with a particular vehicle.

Optionally, some embodiments of the invention may comprise a speed and acceleration detection system. Some embodiments may comprise an imaging system to record an image of at least a part of the passing vehicle or read an identification tag on the vehicle in order to identify the vehicle. Some embodiments of the invention may provide a system and method for reliably and accurately determining the temperature of portions of a passing vehicle.

Another embodiment of the invention provides an unmanned bunkered emission detection system and method that may be operated unattended and may provide a rugged and unobtrusive roadside emission monitoring system.

DETAILED DESCRIPTION OF THE PREFERRED EMBODIMENTS

Figure 1:
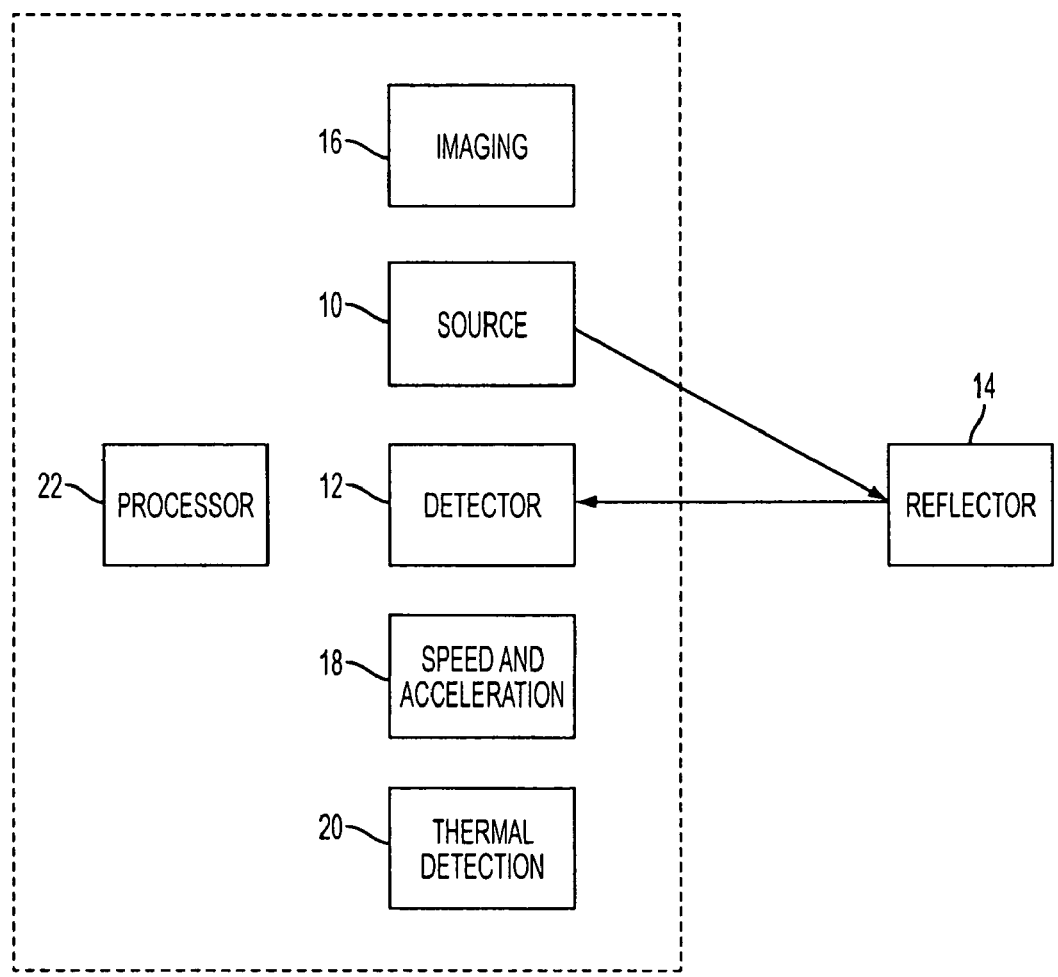
FIG. 1 shows a schematic block diagram of components of an embodiment of a remote emission detection system.

FIG. 1 shows a schematic representation of components of the remote emissions sensing, device (RSD). Embodiments of the invention may include some or all of the various components as described below.

Radiation Source

Preferably, an RSD comprises a source of electromagnetic radiation 10 which may be used in the absorption spectroscopy measurement of various components of vehicle exhaust emissions. Preferably, source 10 may comprise an infrared (IR) radiation source. Some embodiments of the RSD may include other types of radiation sources for example, an ultraviolet (UV) source, a visible light source, or a combination of radiation sources.

Radiation Detector

The RSD may further comprise a detector array 12 for detecting radiation. The detector array 12 is preferably chosen to permit detection of electromagnetic radiation emitted by the source 10. For example, detector array 12 may comprise a photodetector (e.g., a photodiode), a photomultiplier tube (PMT), a spectrometer or any other suitable radiation detector. For example, a mercury cadmium telluride (Hg—Cd—Te) photodetector may be used to detect IR radiation. Other suitable detectors or detector arrays 12 may also be used.

According to an embodiment of the invention, the RSD may comprise a single detector with multiple filters instead of an array employing multiple detectors. The multiple filters may be moveable, such as spinning filters, to allow multiple components to be detected. In this manner, a single detector can be employed to detect a plurality of different exhaust components because each of the moveable filters is designed to allow only the wavelength band of interest for a particular exhaust component to pass to the detector. According to another embodiment of the invention, the RSD may comprise a spectrometer, or other detecting device which may be used to detect more than one component.

Reflector

Preferably, the RSD may comprise a reflector 14 mounted in a manner to allow radiation from the source 10 to be reflected to the detector array 12 for analysis. The reflector 14 may comprise a mirror, flat mirror, lateral transfer mirror (LTM), vertical transfer mirror (VTM), retroflector, or other device. In one embodiment the reflector 14 may comprise a lateral transfer mirror to reflect radiation from the source 10 along a path displaced laterally or vertically, depending on orientation, from the incident direction.

Imaging Unit

The RSD may include an imaging unit 16 to capture and/or record an image of a vehicle passing by the RSD. The imaging unit 16 may be arranged to record an image of a vehicle at a specified location relative to the detection system. The imaging unit 16 may comprise, for example, a camera, such as a film, video or digital camera. Other imaging devices may also be used.

Preferably, the imaging unit 16 may record an image of the vehicle identification tag (i.e., license plate). Tag information may be processed, using a suitable data processor, to provide additional information about the vehicle. For example, Motor Vehicle Department databases may be accessed to retrieve owner information, make, model type, model year and other information. In some embodiments, this additional information may be incorporated into the emission sensing data analysis. For example, the make and model year of the vehicle may be used to determine input information for certain processing steps, including information such as whether the vehicle includes a carburetor or fuel injector, whether the car runs on diesel fuel or gasoline, etc.

Speed and Acceleration

The RSD may also include a speed and acceleration detection unit 18. Preferably, a vehicle's speed and/or acceleration may be measured as it passes the RSD using speed detection unit 18. For example, the speed and acceleration detection unit 18 may comprise an arrangement of laser beams or other light beams associated with timing circuitry. According to an in embodiment of the invention, the laser or light beams may be arranged to traverse the path of a vehicle at various points. As a vehicle passes, it will cause interruptions in the laser or light beams. The times at which the beam interrupts occur may be used to calculate the vehicle's speed and/or acceleration. Other methods of determining vehicle speed and/or acceleration may also be used.

According to another embodiment of the invention, the laser or light beams may be arranged to traverse the path of a vehicle at a single point in the vehicle's path. For example, radar systems may be used to determine vehicle speed and acceleration. Alternatively, transducers. piezoelectric elements, or other "drive over" detectors may be placed at locations in the roadway to monitor vehicle passage. Preferably, speed and/or acceleration data may be input into a data processing unit 22 to help characterize vehicle operating conditions (e.g., accelerating or decelerating) or to be used to determine which vehicle is to be associated with a particular sensor measurement. Other uses of the speed and acceleration data are also possible.

Thermal Detection Unit

Some embodiments of the invention may incorporate a thermal to detection unit 20. Preferably, the thermal detection unit 20 may comprise a non-contact thermometer system. For example, an IR thermometer may be used to optically detect the temperature of remote objects. Other temperature detection systems may also be used.

Preferably, the thermal detection unit 20 is used to detect the temperature of portions of the vehicle passing through the RSD. Some embodiments may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat of the passing vehicle which is reflected from the roadway surface.

Preferably, the thermal information recorded by the thermal detection unit 20 may be used to indicate that the engine has just recently been started (i.e., the engine is "cold" or has not reached normal operating temperature). Such a cold engine reading may be used, for example, to initiate an alternative data processing routine. Certain embodiments of the present invention may reduce the chance of a potentially misleading reading by also detecting the temperature of other portions of the vehicle. Other uses for collected thermal data are also possible.

Figure 2:
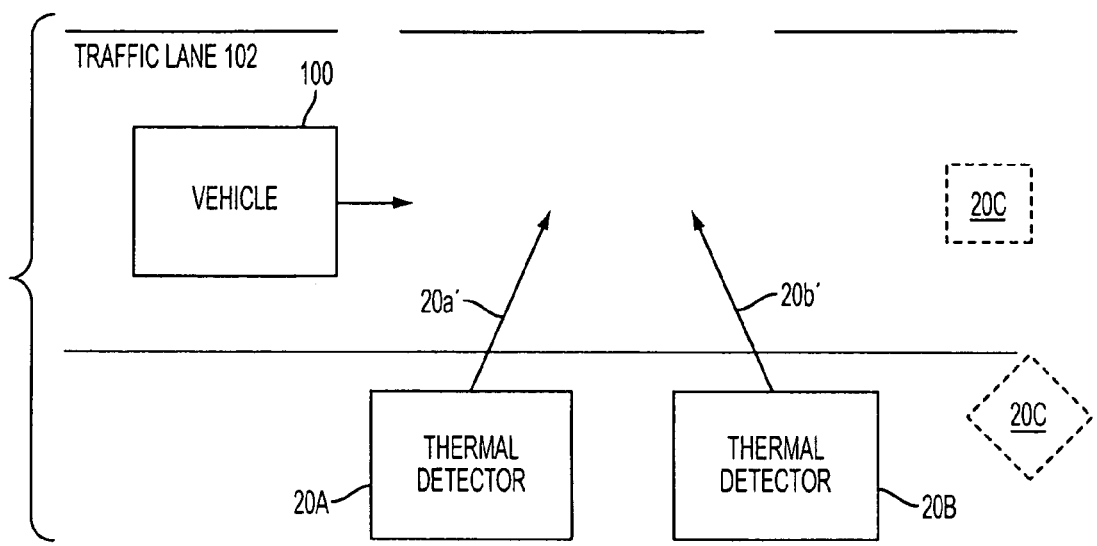
FIG. 2 shows a schematic block diagram of an embodiment of a thermal detection unit.

Thermal detection unit 20 may comprise various detection apparatus configurations. For example, FIG. 2 depicts a thermal detection system that may be incorporated into an embodiment of the RSD. As shown, two thermal detectors 20A, 20B are arranged to detect a vehicle 100 travelling in a traffic lane 102. Preferably, the thermal detectors 20A, 20B are positioned at points affording different angles of view 20a', 20b' at vehicle 100. For example, the thermal detectors 20A, 20B may be positioned near the locations of speed and acceleration detection units (i.e., spaced with some distance between detectors). Spatial separation of the detectors 20A, 20B and the differing angles of view 20a', 20b' increase the likelihood of detecting the temperature of the areas of interest on the vehicle (e.g., the engine, catalytic converter, etc.) and also afford a time sequence of measurements since the vehicle passes one detector, then the other at a later time. In some embodiments, an additional thermal detector 20C may be incorporated into the RSD. Detector 20C may be positioned at a suitable location to detect the temperature of the front of the vehicle (e.g., the radiator or engine). For example, detector 20C may be positioned at either side of the lane 102, at a sufficient height to detect the front of the vehicle, or detector 20C may be embedded into lane 102 to record a head-on view of an oncoming vehicle.

Figure 3:
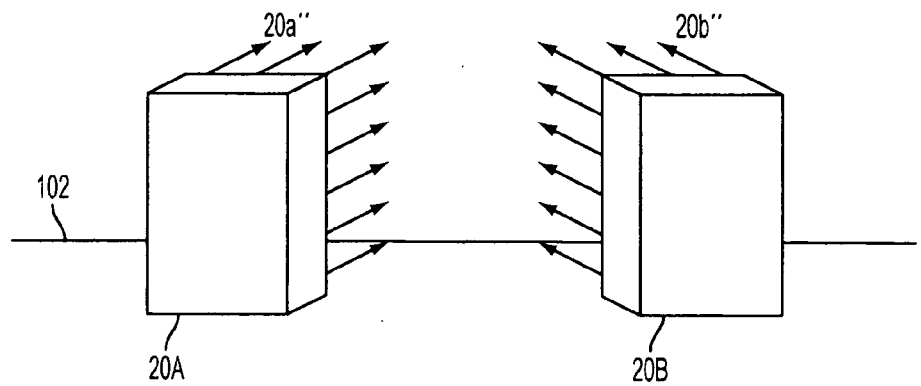
FIG. 3 shows a schematic block diagram of an alternative embodiment of a thermal detection unit.

Some embodiments of the invention may include arrays of thermal detectors to increase the likelihood of obtaining the desired temperature readings. For example, in an embodiment incorporating an IR thermometer, an array of detection beams 20a", 20b" may be aimed at the vehicle 100. The array may span vertical and horizontal regions, as shown in FIG. 3. Using such an array of detection beams allows the thermal detection unit 20 to detect the temperature of vehicles of varying size and shape. In addition, some of the beams in the array may be used to detect reflected heat off of the road surface of lane 102.

Using an array of detector beams 20a", 20b" may also provide greater precision in temperature measurements. The focal point of each detection beam in the array can be narrowed to detect the temperature of a small region of interest. In this manner, a more precise temperature reading for each point may be obtained. For example, a detector beam with a focal point four inches in diameter will take an average temperature over the whole four inch region within the focal point. If the region of interest happens to be a one inch exhaust pipe on a vehicle, the detector will average the temperature of the region of interest (i.e., the pipe comprising one-fourth of the focal region) with objects outside of the region of interest (i.e., the other three fourths of the focal region). In contrast, an array of smaller focal point detector beams (e.g., one inch in diameter each), if properly aligned, will be more likely to provide a precise temperature reading for a small region of interest.

Processing Unit

The RSD preferably includes a data processing unit 22. The data processing unit 22 may include a suitable processing device, for example, a computer or other microprocessor. The data processing unit 22 may optionally employ software to accomplish desired analysis of collected and/or stored data. For example, software may be used to calculate the relative amounts of various exhaust gas constituents, concentrations of various exhaust gas constituents (e.g. HC, $CO_2$, $NO_x$, CO, etc.), the decay rate (e.g., dissipation in time) of the exhaust constituents, the opacity of the exhaust plume, the temperature, speed and acceleration of the vehicle, and to determine other desirable information as well.

In a preferred embodiment, data processing unit 22 is employed to calculate the relative amounts of various exhaust gas constituents by computing the ratio of the absorption for a particular exhaust gas constituent to the $CO_2$ absorptions. This preferred method eliminates the need to calculate the total amount of exhaust plume present since the calculated ratios alone provide sufficient information to identify vehicles which do not meet predetermined pollution criteria. Also, should the calculation of absolute concentrations of various components be required, an estimated value of $CO_2$ concentration based on vehicle type, fuel type, calibration readings or other methods, may be employed for this purpose.

The data processing 29 unit may also comprise software to accomplish other data analysis functions. For example, vehicle emission data may be checked for running losses. Running losses may typically include emission readings due to fuel system leaks on a vehicle (e.g., leaky fuel tank filler cap, fuel line, etc.), blow-by emissions (i.e., crank case emissions blowing by the piston rings), emissions due to other vehicles in the vicinity or other systematic losses.

The data processing unit 22 may also include software to accomplish various vehicle owner notification functions. For example, the owner of a vehicle that has been recorded as being in compliance with certain predetermined emission levels may receive a notification. Coordination with local authorities may be arranged to grant vehicle owners a waiver or pass of local emission certification procedures upon receiving such a notification. Likewise, vehicles that fail to meet predetermined emission levels may receive a notification requiring the owner to remedy the non-compliance. Other data processing functions are also possible.

According to one embodiment, the emission detection may be performed by a remote sensing device, such as RSD-1000™ or RSD-2000™, manufactured by RSTi, Tucson, Ariz., wherein the detection apparatus and process control software is modified to perform the novel functions set forth herein.

Multilane RSD Unit

The invention comprises a multilane RSD that permits the detection of vehicle emissions at locations where vehicles may be traveling in multiple substantially parallel traffic lanes. Several configurations for multilane RSD's are described below. The term "multiple traffic lanes" as used herein means two or more lanes of traffic, and includes two or more lanes of traffic with vehicles in different lanes travelling in the same or opposite directions.

One embodiment of a multilane RSD comprises components as shown in FIG. 1. In this embodiment, a reflector 14 may be positioned opposite a detector array 12 across a multiple lane roadway. In any embodiment of the invention, a single detector can be substituted for the detector array 12. The single detector may be used to detect a single species of interest, or it may be used in combination with a plurality of moveable filters to detect a plurality of different species of interest. In this embodiment, the moveable filters are selected such that each filter passes a band of radiation to the detector substantially centered about the characteristic wavelength of a particular species of interest. In this manner, a single detector can be used to detect a plurality of different exhaust components by passing the radiation through a different filter for each exhaust component. For those embodiments using an active source, source 10 may also be positioned opposite reflector 14 such that the radiation proceeds from the source 10 to the reflector 14 and then to the detector array 12.

Multilane RSD embodiments where the detector array 12 and the reflector 14 are separated by more than one vehicle lane may use one of several techniques to identify which vehicle corresponds to a particular set of emission data. For example, data processing software may be used to create a decay rate curve for a given exhaust plume. The decay rate may preferably be based upon dissipation characteristics for some exhaust constituents (e.g., HC, $CO_2$, CO, $NO_x$, etc.). Comparison of these dissipation characteristics for a given exhaust plume with known or predicted standard curves can be used to determine whether the given plume is from more than one emission source. For example, if two vehicles happen to pass through the multilane RSD in close proximity, the exhaust plume decay rate curve will usually contain two distinct decay rates indicating the presence of two vehicles. If the decay curves for multiple vehicles cannot be distinguished, alternative data processing procedures may be used. For example, the data may be discarded as invalid, the vehicles may be identified for later testing or other alternative procedures for associating a particular vehicle with a particular exhaust plume may be initiated.

Figure 4:
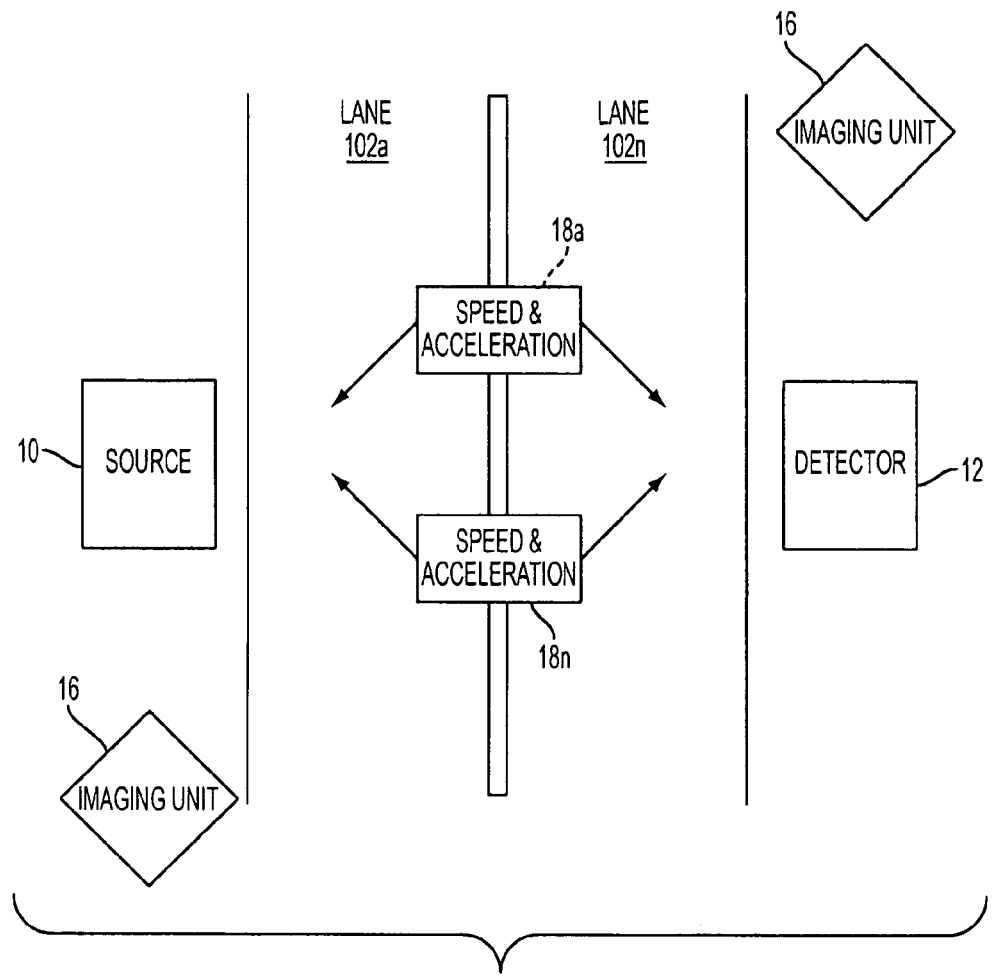
FIG. 4 shows a schematic block diagram of an embodiment of the invention incorporating a speed and acceleration detection unit.

Another embodiment of the multilane RSD may comprise using speed and acceleration unit 18 and/or imaging unit 16 to assist in identifying which vehicle corresponds to a detected exhaust plume. Several configurations are described with reference to FIG. 4. One embodiment coordinates vehicle imaging data with detected plume emission data to correlate vehicles and plumes. For example, a source 10 and detector array 12 may be aligned to span a multilane roadway, of which two lanes, 102a, 102n, are shown (another configuration may comprise source 10 and detector array 12 on one side of the roadway with reflector 14 on the other, as shown, for example, in FIG. 1). Speed and acceleration units 18a, 18n may preferably be mounted in between lanes 102a, 102n and oriented to record speed and acceleration data for a single one of lanes 102a, 102n. For example, speed and acceleration units 18a, 18n may comprise laser beams projecting into one lane or the other, transducers, piezoelectric devices, or other "drive over" detectors embedded in each lane or radar guns aimed at the respective lanes. In this manner, individual speed and acceleration data for each vehicle can be obtained and matched with emission data. For example, the speed and acceleration unit 18a for lane 102a may record a vehicle speed at a time just before the unit 18n for lane 102n records vehicle speed and acceleration. Then the first occurring emission data may be associated with the vehicle in lane 102a and the second with the vehicle in lane 102n.

Other embodiments may achieve the same differentiation of vehicles using an imaging unit 16. For example, imaging units 16 may be arranged to view vehicles traveling in a specific lane 102a, 102n (or in a specific direction of travel for lanes with traffic flow in opposite directions). In this manner, recorded vehicle image data may be associated with recorded emission data. For example, a vehicle traveling in lane 102a may have its image recorded moments before a vehicle traveling in lane 102n, then the first occurring emission data may be associated with the vehicle in lane 102a and the second with the vehicle in lane 102n. Other embodiments, comprising various combinations of speed and acceleration units 18 and imaging units 16, are also possible.

Figure 5:
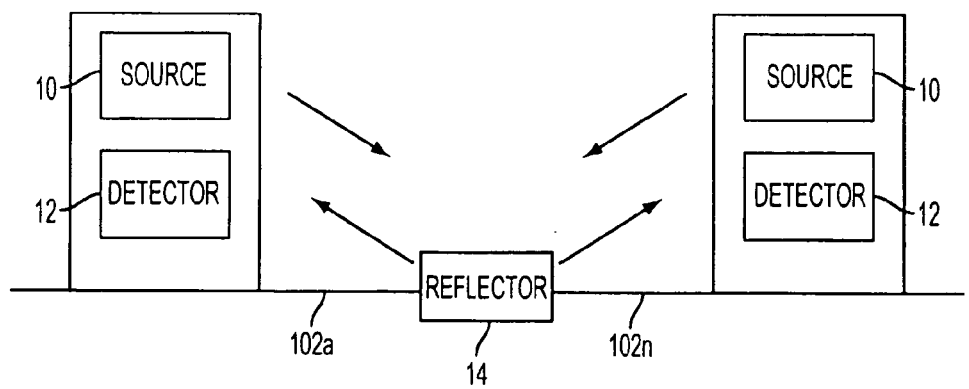
FIG. 5 shows a schematic block diagram of an embodiment of a multilane remote emission detection system.

A further embodiment of the multilane RSD is shown schematically in FIG. 5. As shown, this embodiment may comprise a source 10 and a detector array 12 positioned on the side of each lane 102a, 102n of a roadway. For this configuration emission sensing is preferably accomplished for a two lane roadway. However, sensing across more than two lanes may be possible at a suitable roadway location. In one embodiment a reflector 14 may be positioned in the roadway. Positioning reflector 14 in the roadway may provide a reliable, unobtrusive, safe and sturdy reflector that does not present an impediment or hazard to vehicular traffic. Preferably, reflector 14 may be positioned between lanes 102a, 102n. Other locations are possible. Preferably, the reflector 14 may be located in a manner to cause the reflected radiation to intersect the exhaust plume of a vehicle. For example, a reflected radiation beam height of approximately twelve (12) to eighteen (18) inches from the road surface, in the middle of each lane 102a, 102n, should be sufficient to intersect most vehicle exhaust plumes. In this manner, each source 10 and detector array 12 will record emission data for one lane (e.g., 102a, 102n). In some embodiments, it may be preferable to incorporate speed and acceleration unit(s) 18 and reflector(s) 14 into the same location (e.g., in between lanes 102a, 102n).

Figure 6:
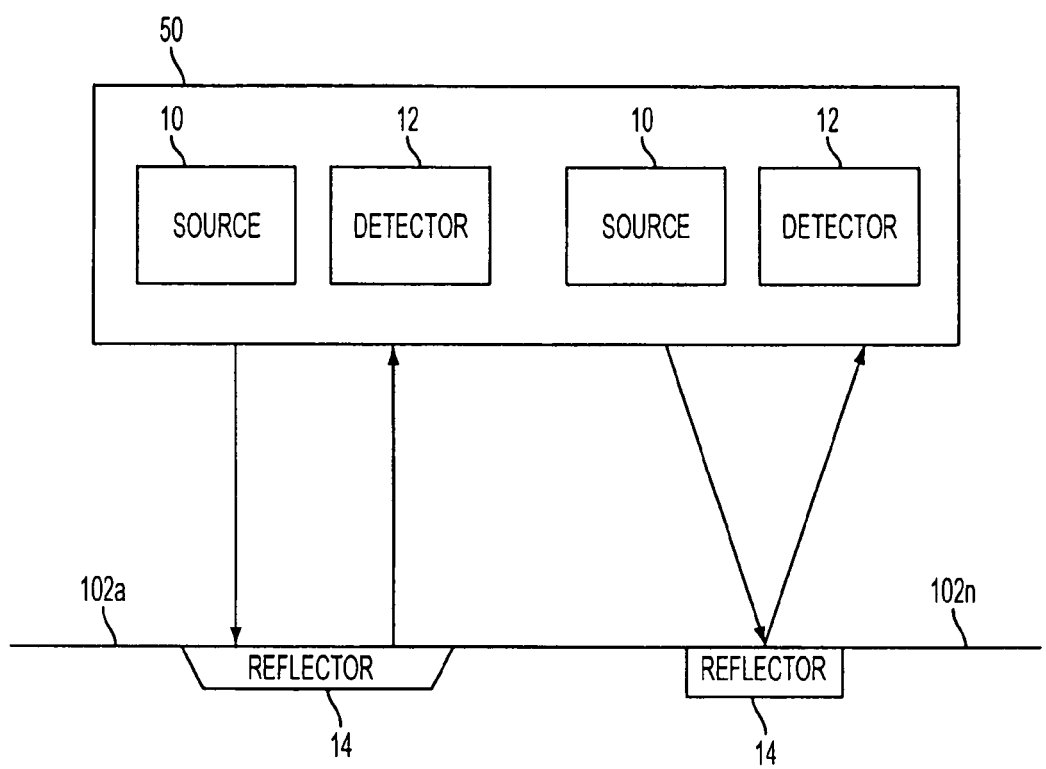
FIG. 6 shows schematic block diagram of an embodiment of a multilane remote emission detection system.

FIG. 6 shows yet another embodiment of the multilane RSD employing an overhead mounting configuration. Sources 10 and detector array 12 may preferably be positioned above a roadway. Any suitable overhead location 50 may be chosen for sources 10 and detector array 12. For example, overhead location 50 may comprise a highway sign, toll booth, overpass, bridge or similar location. In this embodiment, reflectors 14 may be mounted in the roadway, for example, in each lane 102a, 102n. In this manner, emission data may be recorded for vehicles in each lane 102a, 102n.

According to a further embodiment of the invention, multiple instruments for each lane may be used to measure vehicle emission. Each lane of a road may have two or more instruments to measure vehicle emission, thereby allowing more accurate results to be achieved. By way of example, multiple instruments may be placed side-by-side and positioned such that radiation from each instrument passes through the same exhaust plume at substantially the same time. By way of another example, multiple instruments may be placed in series and positioned such that radiation from each instrument passes through the exhaust plume from a single vehicle at different times. Other methods using multiple instruments in the same lane may also be used.

Bunkered Unit

Figure 7:
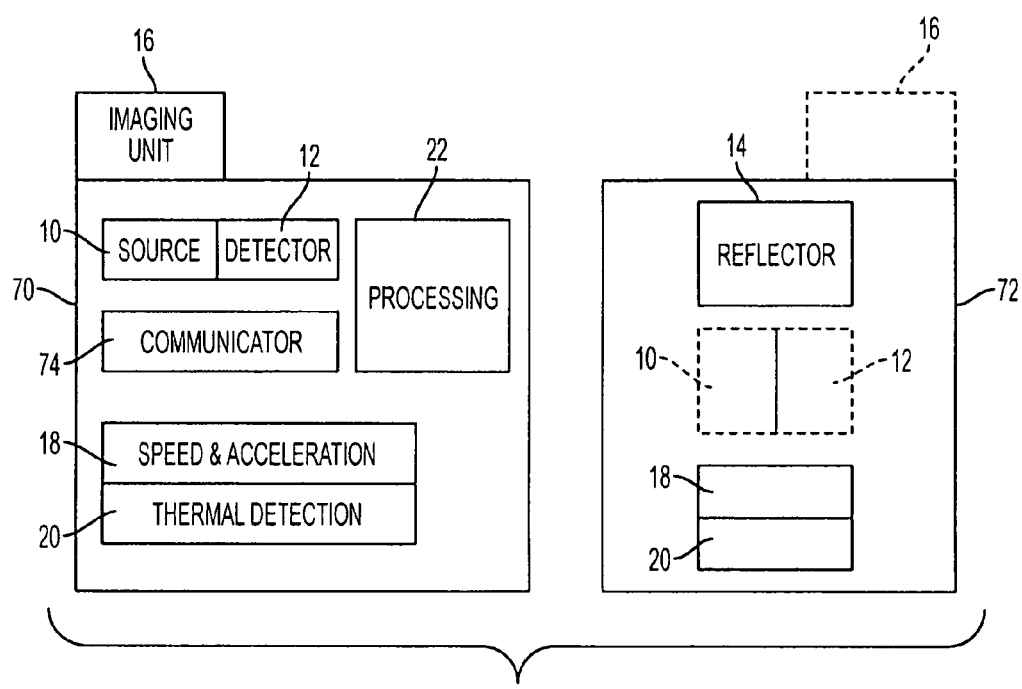
FIG. 7 shows a schematic block diagram of a bunkered remote emission detection system.

A still further embodiment of the invention comprises a compact, unmanned RSD that may be used for unattended monitoring of vehicle emission data (also referred to as a "bunkered" unit). FIG. 7, schematically depicts one possible bunkered unit. In the embodiment shown, the RSD components are packaged into two groups 70, 72. Group 70 may preferably comprise source 10, detector array 12, data processing unit 22, imaging unit 16 components of speed and acceleration unit 18 and thermal detection unit 20 and communicator 74. Group 72 may comprise reflector 14, and components of speed and acceleration unit 18 and thermal detection unit 20. Components of speed and acceleration unit 18 and thermal detection unit 20 are depicted as split between the two groups 70, 72 to represent units 18 and 20 that span a roadway lane(s) (e.g., a speed and acceleration unit 18 may comprise a comprising laser beam and sensors to detect the laser beam). Other embodiments may not require splitting speed and acceleration unit 18 and thermal detection unit 20. In such embodiments the units 18 and/or 20 may be located entirely in one of groups 70, 72. In some embodiments, the speed and acceleration unit(s) 18 may be placed in close proximity to the data processing unit 22. For example, the speed and acceleration unit 18 may be placed within five (5) feet of the data processing unit 22. Other groupings of components may be possible. For example, as indicated in dashed lines, imaging unit 16 may be located at other locations (e.g., with group 72). In addition, some embodiments may comprise a source 10 in one group and a detector array 12 in another, thus, eliminating the need for a reflector 14. Such an arrangement is indicated by the dashed source 10/detector array 12 included with group 72. Communicator 74 may communicate information, such as measured vehicle emissions and identification tag information, from RSD. Communicator 74 may communicate by a wire connection, such as cable or telephone line, or a wireless connection, such as by a radio, cellular, satellite transmitter or other types of suitable wireless communication. Information may be communicated to another location for storage, processing, viewing, or other use of the information. Other types of communication may also be used.

Figure 8:
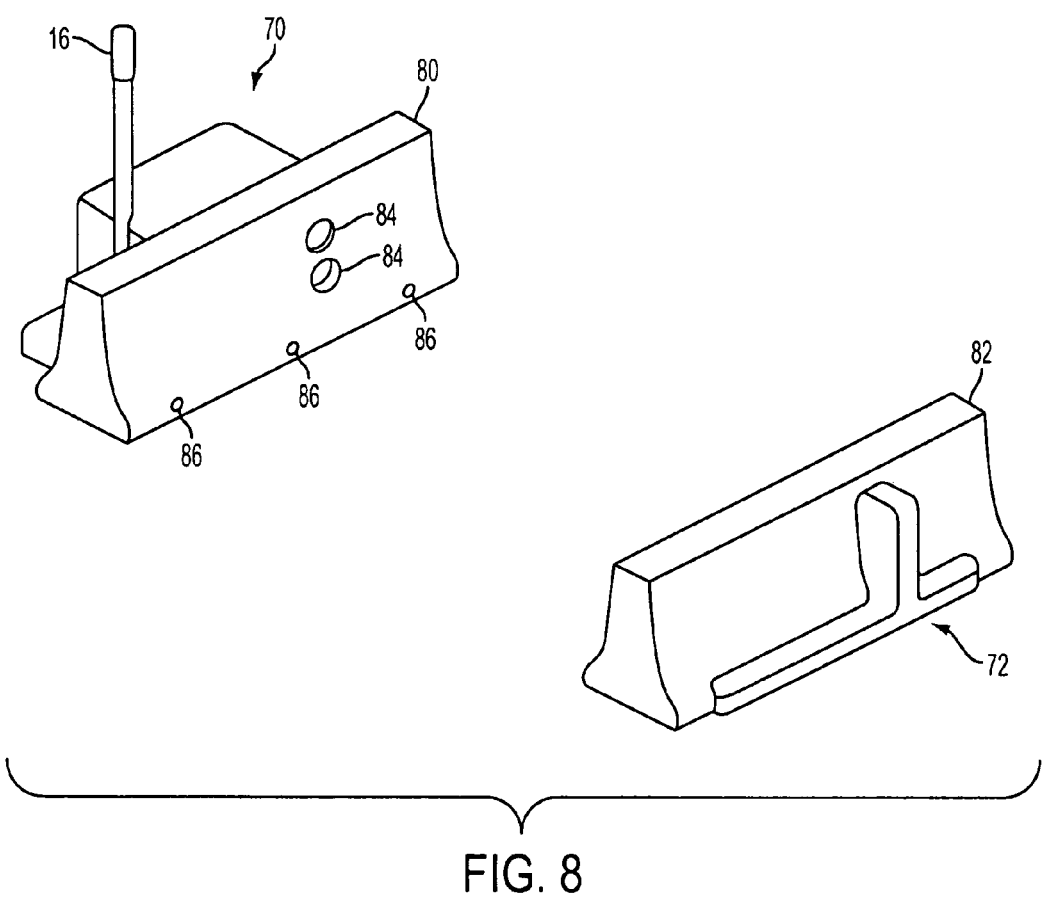
FIG. 8 shows a perspective view of an embodiment of a bunkered remote emission detection system.

One embodiment of the grouped or bunkered unit may comprise incorporating one or more RSD's into existing roadway structures. Preferably, roadway structures such as toll booths, concrete lane dividers (e.g., Jersey barriers), divided highway barriers and other structures may house one or more RSD's. For example, FIG. 8 depicts an RSD incorporated into concrete lane divider structures 80, 82. As shown in FIG. 8, the structures 80, 82 may include modifications to enable the various components to function. For example, apertures 84 may provide the source 10 and the detector array 12 access to project and receive the emission detection beam. Likewise, apertures 86 may provide speed and acceleration unit 18 and/or thermal detection unit 20 with access to the roadway. Other modifications may be possible.

One embodiment of the bunkered RSD unit may comprise modifications to data routines or software within processor 22. Preferably, these modifications compensate for changes in the sensing routine due to the grouping of components. Moving imaging unit 16 into close proximity with group 70 may cause changes in how the image of the vehicle is recorded. For example, moving imaging unit closer or to group 70 may lengthen the delay required to trigger imaging unit 16 in a timely fashion to record the vehicle being detected. Other changes may also be necessary.

One embodiment of the invention reads an identification tag on a vehicle in order to identify the vehicle and associate particular sensed vehicle emission information with the vehicle. As noted previously, according to an embodiment of the invention, an identification tag may comprise a license plate. An imaging unit 16, such as an automatic license plate reader, may record license plate information to obtain vehicle information. An identification tag comprising a transponder located on or within a vehicle may alternatively be used to identify a particular vehicle and/or obtain vehicle information. A transponder may be located within a tag that is placed within the vehicle (e.g., hung from a rear view mirror, placed on the dashboard, etc.), or that is integral within the vehicle (e.g., part of a global positioning system ("GPS"), located within the engine of the vehicle or elsewhere). A transponder may transmit information about a vehicle, including make and model of the vehicle, engine characteristics, fuel type, the owner of the vehicle, and other information which may be pertinent. According to an embodiment of the invention, a transponder may be used in connection with other functions. By way of example, a transponder may also be used in connection with a toll pass, whereby a driver can electronically pay tolls via the transponder without stopping the vehicle.

An identification tag may also comprise a tag or decal that requires a reader. By way of example only, an identification tag may comprise a decal with identifying marks (e.g., bar codes, infrared markings, etc.) containing information about the vehicle. The decal may be located outside the vehicle, such as on a front or rear bumper, on the under-side of the vehicle, or any other location on the vehicle where the decal may be suitably read. A reader may observe the decal and thereby obtain information about the vehicle. One preferred embodiment employs a bar code placed on the roof of the vehicle which can be read by a reader placed above the vehicle.

A receiver may be used to obtain information from an identification tag. According to an embodiment of the invention, an antenna may receive signals transmitted from an identification tag containing a transponder. Any type of conventional receiver may be used to receive signals. According to an embodiment of the invention, one reader and/or receiver may be used in connection with multiple lanes. Based on the signal received or the decal read, a receiver or reader may determine in which lane a particular vehicle is located at a particular time.

A data processing unit 22 may receive information about a vehicle from a reader and/or a receiver. According to an embodiment of the invention, data processing unit 22 may receive vehicle information. Vehicle information and information obtained by sensing vehicle emissions may be stored. Data processing unit 22 may correlate vehicle information received from an identification tag with the results from vehicle emissions sensing. Data processing unit 22 may update a vehicle record to account for the results obtained by processing vehicle emission data, such as indicating whether a vehicle has passed or failed predetermined emissions criteria.

According to an embodiment of the invention, for a typical two-lane rural freeway, a system may be placed at a roadway overpass on the downstream side of the bridge structure and may consist of a linear array of optical remote sensors looking vertically down at the roadway at predetermined intervals (e.g., approximately two foot intervals). By way of example, for a twenty-four foot wide roadway, thirteen units would look down and onto each side of two twelve foot wide lanes to provide substantially complete coverage of the lanes. The roadway may have embedded in it hard wearing reflectors, exactly level with the road surface so as not to be felt by passing vehicles. By way of example, in a system having thirteen units, there may be thirteen reflectors spaced at approximately two foot intervals below the thirteen detector arrays. Each unit would have an outgoing and a return beam, such as shown in the shape of a close angled V.

The timing of data collection by an array of detectors may be determined and stored by a single master computer. Detector units or detector arrays may return to the master computer a data stream consisting of times and detector voltages or time and calibrated gas absorption measurements. The master computer may generate a time and space indexed array of emissions data. By way of example, at least two beams may be blocked by any vehicle larger than a motor bicycle passing through the beams. The location and timing of all vehicles which pass by may be determined from this beam blocking and any detector arrays which observe exhaust plumes, including those recently unblocked, may be used to obtain emissions data. For a twelve foot wide lane, with detector arrays spaced at two-foot intervals, two beams may be blocked, while five beams may be received at other detector arrays. With this arrangement and a system which keeps accurate timing, it is possible to determine which vehicle a given exhaust plume is coming from, even when two vehicles pass simultaneously in parallel lanes or when exhaust is spread by, for example, turbulence behind vehicles and cross winds.

A plurality of video cameras mounted on a roadside pole upstream of the RSD may be triggered by the beam unblocks (as in the current horizontal beam systems) to capture an image of the rear of a vehicle if individual vehicle information is desired. This concept may be extended to multiple lanes.

Figure 9:
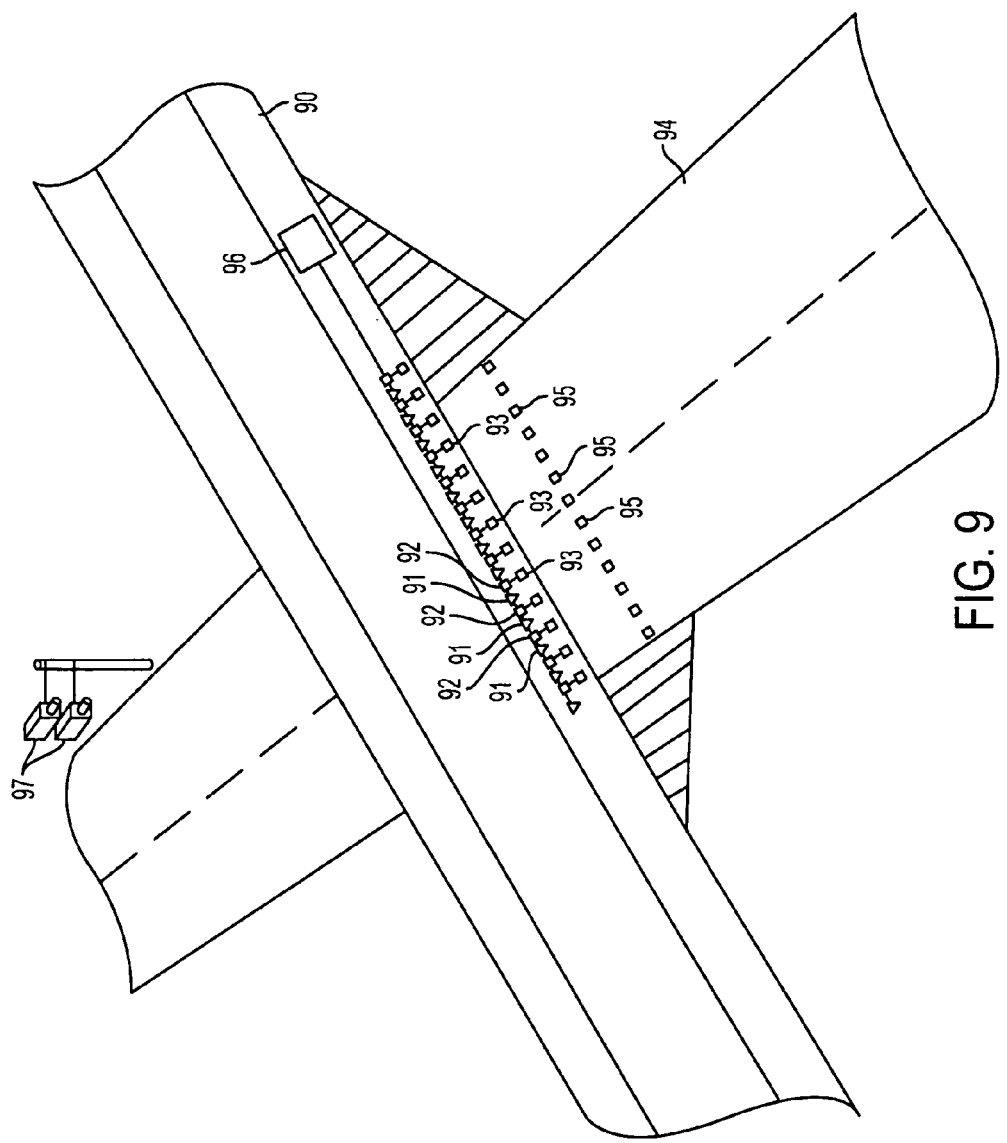
FIG. 9 shows a perspective view of an embodiment of an overhead remote emission detection system.

FIG. 9 illustrates an example of an overhead system according to an embodiment of the invention. An array of light sources 91 and detectors 92 provided with moveable filters 93 may be placed on a bridge structure 90 going over a multi-lane roadway 94. According to an embodiment of the invention, for pollutant measurement including CO, $CO_2$ and HC, infrared radiation may be used for the light sources 91. According to another embodiment of the invention, if NO data are required, a light source combining UV and IR radiation may be used or a diode laser high resolution IR source may be used. Light from each light source 91 may be reflected by a reflector 95 to its individual detector 92. Each detector 92 may measure individually the wavelengths associated with the pollutant measurements desired. According to an embodiment of the invention, each light source 91 and detector 92 may be slaved to a timer of a processor 96 so all events (beam blocks and emissions measurements) have a common time stamp.

Each detector 92 may report events back to processor 96 which may be equipped with specialized software which enables it to discern from the array of time, space, beam block and detector information which vehicle is to be associated with a particular plume measurement. In some cases, plume measurements may be attributed to a plurality of vehicles by processor 96 in which case the plume measurement may be discarded or it may be employed using an alternative calculation to account for the multiple vehicles. Processor 96 may control video cameras 97 so as to capture images of vehicles, if vehicle identification is desired.

According to an embodiment of the invention, each pair of light source 91 and detector 92 may act as an independent on-road measurement unit. Those pairs which see a fully blocked beam may be treated very much like the normal horizontal beam systems. The unblocking of the beam by passage of the vehicle out of the beam may trigger a video camera 97 to take a picture and the various emissions measurements may be compared to measurements taken before the beam block to ensure that the observed exhaust is from that vehicle. Data from a source/detector pair which does not see a beam block may be analyzed by processor 96 to determine if an exhaust plume was seen, and if seen where it occurred in space and time relative to any local beam blocks and unblocks and/or other exhaust plume measurements. Such factors as wind speed, vehicle speed and/or acceleration, and wind direction may enter into such determinations. Determining the source of a particular exhaust plume may require multiple pattern recognition software in certain circumstances.

Light source 91 may be any source of light, such as infra-red radiation. According to an embodiment of the invention, infra-red radiation may be required to have a reasonable brightness at 3–4 micron wavelengths. By way of example, a silicon carbide (SiC) resistively heated source may be used. Other possibilities may include light emitting diodes and diode lasers. With diode lasers, near-IR overtone wavelengths may be used. According to an embodiment of the invention, if NO measurements are required, either a tunable diode laser or a UV source may be used. Other examples of light sources 91 that may be used in connection with the present invention include a hot wire, silicon carbide or other carbide filament, a hot glass/quartz envelope around a filament, or other hot materials such as alumina IR sources. According to an embodiment of the invention, light source 91 temperature may be as warm as possible. By way of example, the SiC light source is preferably maintained at about 1700° K. (1400° C.).

Detectors 92 may include any type of detector meeting required signal/noise criteria. According to an embodiment of the invention, electrically cooled lead selenide detectors may be used. Others types of detectors may also be possible in connection with this invention. Examples of detectors that may be used in connection with the present invention include, lead sulfide, HgCdTe and IbSb. For an IR wavelength range, an IbSB may be used at a temperature of 77 K. (−223C). Lead selenide may be optimally used when cooled to a temperature of 210K (−90C). This low temperature may be hard to achieve thermoelectrically, so a higher temperature may alternatively be used.

According to an embodiment of the invention, reflector 95 on roadway 94 may be a flat mirror so that reflector 95 may be flush with roadway 94. By way of example, a sapphire flat plate with a gold coating on the back of the plate may be used as sapphire is a very tough material and transparent in the IR and UV bands. By way of another example, if UV reflectivity is required, an aluminum coating may be used in place of a gold coating. According to another embodiment of the invention, a full corner-cube retroreflector or a pair of mirrors at right angles may be used to achieve the required beam return to detector 92. Other examples of reflectors 94 that may be used in connection with the present invention include materials which can be front silvered, such that a polished aluminum plate or gold coating could be used. A back silvered material requiring both IR transparency and considerable toughness, or some type of synthetic spinel mineral with a gold or aluminum coating may also be used.

Other embodiments and uses of the invention will be apparent to those skilled in the art from consideration of the specification and practice of the invention disclosed herein. The specification and examples should be considered exemplary only and the scope of the invention should be determined from the claims appended hereto.

What is claimed is:

1. A system for remote sensing of vehicle emissions in a multilane setting with a plurality of vehicle travel lanes, the system comprising:
   at least one radiation source which emits a radiation beam across two or more vehicle travel lanes, and through at least one exhaust plume;
   at least one radiation detector for receiving the radiation beam; and
   at least one processor for determining, based only on emissions data received from the at least one radiation detector, whether the emissions data corresponds to emissions from two or more vehicles.

2. The system according to claim 1, wherein the at least one processor compares a decay rate of the at least one exhaust plume with a predicted decay rate to determine if the at least one exhaust plume is representative of a particular vehicle's exhaust plume.

3. The system according to claim 2, wherein the decay rate is based on dissipation characteristics of constituents of the at least one exhaust plume.

4. The system according to claim 1, wherein the at least one processor compares a decay rate of the at least one exhaust plume with a known decay rate for a particular vehicle to determine if the at least one exhaust plume is representative of that particular vehicle's exhaust plume.

5. The system according to claim 1, wherein the system includes at least one vehicle identification unit operatively connected to the processor and the processor associates detected vehicle emissions data with a specific, identified vehicle, based on information obtained from the at least one vehicle identification unit.

6. The system according to claim 5, wherein the at least one vehicle identification unit is selected from the group consisting of an automatic license plate reader, photographic apparatus, at least one receiver for receiving a vehicle identification signal from a transponder located on a vehicle, and at least one reader which reads vehicle identification information located on a vehicle.

7. The system according to claim 1, further comprising at least one reflector for directing the radiation beam emitted from the at least one radiation source to the at least one radiation detector.

8. The system according to claim 7, wherein the at least one reflector is selected from the group consisting of a mirror, a flat mirror, a lateral transfer mirror, a vertical transfer mirror, or a retroflector.

9. The system according to claim 7, wherein the at least one radiation source and the at least one radiation detector are located directly above a vehicle lane and the at least one reflector is located below or flush with the vehicle lane.

10. The system according to claim 1, wherein the system comprises at least one radiation source and at least one radiation detector per lane in the multilane setting.

11. The system according to claim 1, wherein the system comprises a plurality of radiation sources and a plurality of radiation detectors per lane.

12. The system according to claim 1, further comprising a thermal detection unit for determining the temperature of one or more vehicle components.

13. The system according to claim 1, further comprising at least one speed and acceleration device for determining the speed and acceleration of a vehicle.

14. The system according to claim 13 wherein the at least one speed and acceleration device includes a light beam directed across a lane from any direction.

15. The system according to claim 13, wherein the at least one speed and acceleration device includes a drive over detector.

16. The system according to claim 1, wherein the system is incorporated into existing roadway structures.

17. The system according to claim 1, where the at least one processor is located remotely from the at least one radiation source and the at least one radiation detector, and information from the at least one radiation detector is communicated via wireless communication to the at least one processor.

18. The system according to claim 1, wherein the at least one processor determines which vehicle emissions data corresponds to which vehicle based on a combination of vehicle emissions data in time and space and vehicle identification data.

19. The system according to claim 1, wherein the at least one processor creates a decay rate curve for the at least one exhaust plume.

20. The system according to claim 19, wherein the decay rate curve is based upon dissipation characteristics for at least some exhaust constituents comprising the at least one exhaust plume.

21. The system according to claim 19, wherein a decay rate curve comprising two distinct decay rates indicates that the emissions data from the at least one exhaust plume corresponds to two vehicles.

22. The system according to claim 19, wherein a decay rate curve comprising multiple distinct decay rates indicates that the emissions data from the at least one exhaust plume corresponds to multiple vehicles.

23. A system for remote sensing of a vehicle emissions in a multilane setting including a plurality of vehicle travel lanes, the system comprising:
  at least one radiation source which emits a radiation beam across two or more vehicle travel lanes, and through at least one exhaust plume;
  at least one radiation detector for receiving the radiation beam;
  a plurality of movable light filters;
  at least one reflector for directing the radiation beam from the at least one radiation source to the at least one radiation detector via the movable light filters; and
  at least one processor for determining, based only on emissions data received from the at least one radiation detector, whether the emissions data corresponds to emissions from two or more vehicles.

24. The system according to claim 23, wherein the at least one processor determines which vehicle emissions data corresponds to which vehicle based on a combination of vehicle emissions data in time and space, and vehicle identification data obtained from at least one vehicle identification unit.

25. The system according to claim 24, wherein the system comprises at least one radiation source, at least one radiation detector, and at least one reflector per vehicle travel lane.

26. The system according to claim 23, wherein the system comprises a plurality of radiation sources, a plurality of radiation detectors and a plurality of reflectors per vehicle travel lane.

27. The system according to claim 23, further comprising at least one vehicle identification unit, wherein the at least one vehicle identification unit is selected from the group consisting of an automatic license plate reader, at least one receiver which receives a signal from a transponder located on a vehicle, and at least one reader which reads vehicle identification information located on a vehicle.

28. The system according to claim 23, wherein the at least one radiation source and the at least one radiation detector are located directly above a vehicle lane, and the at least one reflector is located directly below the vehicle lane.

29. The system according to claim 23, wherein the at least one processor creates a decay rate curve for the at least one exhaust plume.

30. The system according to claim 29, wherein the decay rate curve is based upon dissipation characteristics for at least some exhaust constituents comprising the at least one exhaust plume.

31. The system according to claim 29, wherein a decay rate curve comprising two distinct decay rates indicates that the emissions data from the at least one exhaust plume corresponds to two vehicles.

32. The system according to claim 29, wherein a decay rate curve comprising multiple distinct decay rates indicates that the emissions data from the at least one exhaust plume corresponds to multiple vehicles.

33. A system for remote sensing of vehicle emissions in a multilane setting with a plurality of vehicle travel lanes, the system comprising:
  at least one radiation source which emits a radiation beam across two or more vehicle travel lanes, and through at least one exhaust plume;
  at least one radiation detector for receiving the radiation beam; and
  at least one processor for determining, based on emissions data received from the at least one radiation detector, whether the emissions data corresponds to emissions from two or more vehicles, wherein the at least one processor compares a decay rate curve of the at least one exhaust plume, which is based on dissipation characteristics of at least some exhaust constituents comprising the at least one exhaust plume, with known or predicted decay rate curves to determine if the at least one exhaust plume is from two or more vehicles.

34. A system for remote sensing of a vehicle emissions in a multilane setting including a plurality of vehicle travel lanes, the system comprising:
  at least one radiation source which emits a radiation beam across two or more vehicle travel lanes, and through at least one exhaust plume;
  at least one radiation detector for receiving the radiation beam;
  a plurality of movable light filters;
  at least one reflector for directing the radiation beam from the at least one radiation source to the at least one radiation detector via the movable light filters; and
  at least one processor for determining, based on emissions data received from the at least one radiation detector, whether the emissions data corresponds to emissions from two or more vehicles, wherein the at least one processor compares a decay rate curve of the at least one exhaust plume, which is based upon dissipation characteristics for at least some exhaust constituents comprising the at least one exhaust plume, with known or predicted decay rate curves to determine whether the at least one exhaust plume is from two or more vehicles.

* * * * *